United States Patent
Uno

(10) Patent No.: US 9,018,595 B2
(45) Date of Patent: Apr. 28, 2015

(54) 2-D-TOF-PULSE NEUTRON DETECTOR

(71) Applicant: Inter-University Research Institute Corporation, Tasubaki-shi, Ibaraki (JP)

(72) Inventor: Syouji Uno, Tsukuba (JP)

(73) Assignee: Inter-University Research Institute Corporation High Energy Accelerator Research Organization, Ibaraki (JP)

( * ) Notice: Subject to any disclaimer, the term of this patent is extended or adjusted under 35 U.S.C. 154(b) by 64 days.

(21) Appl. No.: 13/887,876

(22) Filed: May 6, 2013

(65) Prior Publication Data
US 2014/0077093 A1    Mar. 20, 2014

(30) Foreign Application Priority Data
Jun. 26, 2012    (JP) ................. 2012-142945

(51) Int. Cl.
*H01J 47/12* (2006.01)
*G01T 3/00* (2006.01)
*A61N 5/10* (2006.01)

(52) U.S. Cl.
CPC ................. *G01T 3/005* (2013.01); *G01T 3/008* (2013.01); *A61N 2005/109* (2013.01)

(58) Field of Classification Search
CPC ........................................................ H01J 47/12
USPC ...................................... 250/390.08
See application file for complete search history.

(56) References Cited

U.S. PATENT DOCUMENTS

2013/0068956 A1 *    3/2013    Friedman ................. 250/382

FOREIGN PATENT DOCUMENTS

| JP | 2001-508935 A | 7/2001 |
|---|---|---|
| JP | 4280833 B2 | 6/2009 |
| JP | 4613319 B2 | 1/2011 |

OTHER PUBLICATIONS

Klein, Martin et al., "CASCADE, neutron detectors for highest count rates in combination with ASIC/FPGA based readout electronics", Nuclear Instruments and Methods in Physics Research A, vol. 628, 2011, pp. 9-18.
Shoji M., et al., "Development of GEM-based detector for thermal neutron", JINST, 2012, pp. 1-10.

* cited by examiner

*Primary Examiner* — David Porta
*Assistant Examiner* — Hugh H Maupin
(74) *Attorney, Agent, or Firm* — Westerman, Hattori, Daniels & Adrian, LLP

(57) ABSTRACT

[Problem to be Solved] The present invention presents a 2-D-TOF-pulse neutron detector which is able to measure accurate energy spectra, doses, 2-D incident positions and transmission image by measuring TOF of pulse neutron for BNCT and to display the result of the measurement on the transmission image.
[Solution to Problem] The 2-D-TOF-pulse neutron detector includes a GEM-detector being put in a chamber filled with electrolytic-dissociative gas, 2-D-TOF readout integrated circuit and image processor.

1 Claim, 5 Drawing Sheets

2-D-TOF-PULSE NEUTRON DETECTOR

TECHNICAL FIELD

The present Invention presents a two-dimensional-time-of-flight-pulse neutron detector which is able to measure real-time energy-spectra, doses, two-dimensional irradiation-positions and transmission image of pulse neutron for BNCT and to display the result of the measurement on the transmission image.

BACKGROUND ART

Recently, low-energy pulse neutron has been watched as the radiation-source for an advanced neutron medical treatment such as BNCT (boron neutron capture therapy). It has been known that the neutron for BNCT, epithermal neutron being generally in the region of 1 eV~10 keV and thermal neutron being generally 0.5 eV or less, are effective.

For the above neutron, continuous wave (non-pulse) neutron produced with a nuclear reactor has been conventionally used. However, the nuclear reactor cannot be installed in hospitals due to its huge size. On that account, an attempt to use pulse neutron which can be produced with an accelerator has been recently watched.

Methods and apparatuses which are able to measure and monitor accurate energy-spectra, doses, irradiation positions and transmission image of pulse neutron for BNCT have been demanded.

For example, the method and apparatus to measure energy spectra of pulse neutron with TOF (time-of-flight) have been presented (Non-Patent Document 1).

Non-Patent Document 1 have disclosed the CASCADE neutron-detector equipping GEM (gas-electron multiplier) coated with $^{10}B$ and CIPix-ASIC and FPGA as the microprocessor. The documents have disclosed the relationship between the wavelength of neutron vs detection-efficiency of GEM which was measured by TOF using a neutron-source of the neutron beam line CT2-PF1-A. The documents have reported that an energy spectrum of neutron being in the range of 1.8 Å~25 Å in wavelength was measured at a TOF-range of 1 ms~23 ms. The wavelength of 1.8 Å~25 Å can be converted into kinetic energy and velocity, 1.8 Å: $2.53 \times 10^{-2}$ eV, 2,200 m/sec ; 25 Å: $1.3 \times 10^{-4}$ eV, 11.4 m/sec; respectively, which is corresponding to those for so-called cold neutron. Neutron produced with the above CT2-PF1-A (the neutron beam line at J-PARC) was Neutron produced by radiating accelerated proton beam upon a target material. Neutron has contained cold neutron, thermal neutron and epithermal neutron and the like. However, neutron which has been measured with the CASCADE neutron-detector described in the document was only cold neutron in a TOF-range of 1 ms~23 ms. Therefore, it is recognized that the CASCADE neutron-detector disclosed in the document could measure only cold neutron.

As described above, a neutron detector which is able to measure and monitor precise energy spectra, doses, irradiation positions and transmission image of pulse neutron for BNCT have been demanded. However, the detector as achieving such demand has been scarcely known.

CONVENTIONAL ART

Patent Document

[Patent Document 1] JP-A-2001-508935
[Patent Document 2] JP-B-4280833
[Patent Document 3] JP-B-4613319

[Non-Patent Document]

[Non-Patent Document 1] Martin Klein, Christian J. Schmidt, Cascade, neutron detectors for highest count rates in combination with ASIC/FPGA based readout electronics, Nuclear Instruments and Methods in Physics Research A 628 (2011) 9-18

DISCLOSURE OF THE INVENTION

Problems to be Solved by the Invention

An object of the present invention is, in view of the above described circumstances, to provide a new 2-D-TOF-pulse neutron detector which is capable of real-time measurement of energy-spectra, doses, 2-D irradiation positions and transmission image of pulse neutron for BNCT and of displaying the result of the measurement on the transmission image in real-time.

Measure for Solving the Problem

As the result of extensive studies to achieve the above described object, the present inventors have found that the TOF measurement of pulse neutron using GEM is very effective and have achieved the present invention based on this finding.

SUMMARY OF THE INVENTION

That is, in order to achieve the above object, the present invention is: A 2-D-TOF-pulse neutron detector, comprising: a chamber filled with electric-dissociative gas; a GEM detector having a drift electrode, plural GEM-boards and a 2-D-TOF readout electrode, which is included in the chamber; wherein, the drift-electrode to generate electric field is placed at the uppermost part of the GEM detector; the GEM-board having microscopic through-pores and neutron-converting material layer on the surface to convert neutron to α-ray and to generate electrons from the electric-dissociative gas through ionization effect of α-ray and successively to multiply the generated electrons in the microscopic through-pores applied with the electric field, is placed under the drift-electrode; the 2-D-TOF readout electrode to detect electrons, is placed under the bottom GEM-board; a 2-D-TOF readout integrated circuit mounting an ASIC-unit, FPGA-unit and time-clock electronic circuit housed in the FPGA, which is connected with the 2-D-TOF readout electrode; wherein, the ASIC-unit including a 2-D-TOF readout electronic circuit to readout TOF, dose and 2-D incident position of pulse neutron, is connected with the 2-D-TOF readout electrode; the FPGA-unit to perform digital calculation of TOF, dose, 2-D incident position and transmission image, is connected with the ASIC-unit; the time-clock electronic circuit to calculate TOF of pulse neutron by means of independent free-setup, is housed in the FPGA; an image processor to perform high speed-calculation of image data processing; whereby, the measurement of energy spectra, doses, 2-D-incident positions and transmission image of pulse neutron in the range of 1 eV~100 keV is performed in the TOF-range of 0.1μs~200μs, detection of $10^8$ neutrons/sec/cm$^2$ is performed in the TOF-range and displaying the result of the measurements is performed in real-time.

Advantages of the Invention

The present invention is able to perform the real-time measurement of energy spectra, doses, 2-D incident positions and transmission image of pulse neutron in the range of 1 eV~100 keV. The TOF-range, time-resolution and position-resolution performed through the present invention are 0.1 μs~200 μs, about 10 ns and about 0.5 mm, respectively. The present invention is also able to display the result of the measurement on a 2-D-transmission image of a subject.

DETAILED EXPRESSION OF THE INVENTION

Figure 1:
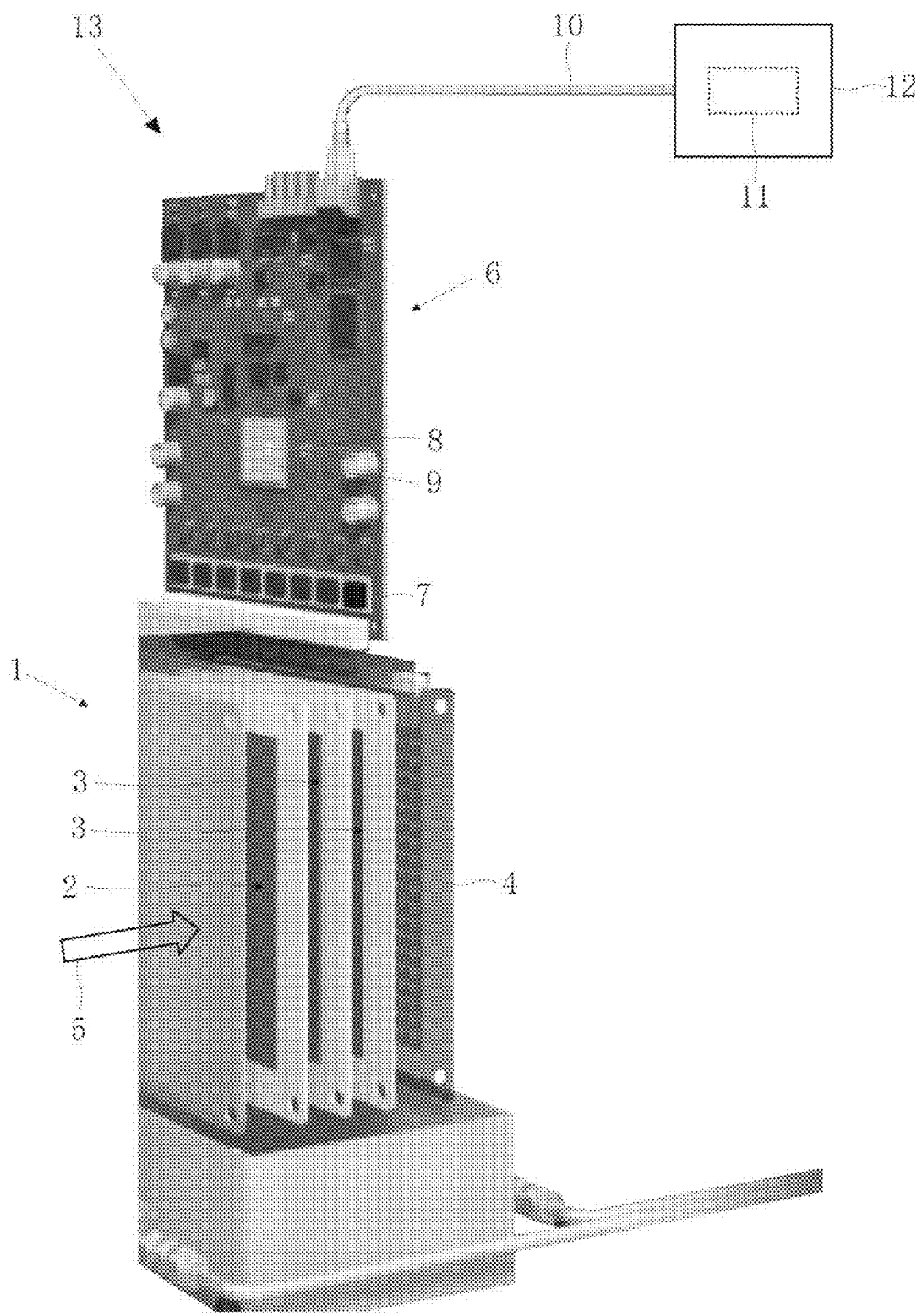
FIG. 1 is a schematic structural view illustrating the 2-D-TOF-pulse neutron detector comprising the GEM-detector, the 2-D-TOF readout integrated circuit and image processor according to the present invention.

The present invention is the 2-D-TOF-pulse neutron detector which is able to perform the real-time measurement of energy spectra, doses, 2-D incident positions and transmission image of pulse neutron for BNCT by mean of TOF-measurement and a display of the result of the measurement on the 2-D-transmission image of a subject.

Pulse neutron for BNCT which can be determined by the present invention is in the range of 1 eV~100 keV.

Pulse neutron for BNCT which can be determined by the present invention is usually produced with an accelerator: whereby, accelerated proton beam is radiated on a target, primary neutron is produced, followed by moderating the primary neutron with a moderator.

Kinetic energy, wavelength, velocity and time-of-flight/1 m-length of pulse neutron are related with the formulas (1) and (2) as follows:

$$E = 0.5\,mv^2 \quad (1)$$

where, E is kinetic energy, m is mass of neutron (m=1.67492735174×10$^{-27}$ kg) and v is velocity.

$$\lambda = h/mv \quad (2)$$

where, λ is wavelength (de Broglie wavelength), h is the Plank constant, m is mass of neutron, and v is velocity. Time-of-flight/1 m-length (T) is given as a reciprocal number of v which is calculated from the formula (1). Therefore, E of pulse neutron in the range of 1 eV~100 keV is related to v, λ and T as follows:

E=1 eV: v=1.4×10$^4$ m/sec, λ=0.2846 Å, T=70 μs
E=10 eV: v=4.4×10$^4$ m/sec, λ=0.09 Å, T=23 μs
E=100 eV: v=1.4×10$^5$ m/sec, λ=0.02846 Å, T=7 μs
E=1 keV: v=4.4×10$^5$ m/sec, λ=0.009 Å, T=2.3 μs
E=10 keV: v=1.4×10$^6$ m/sec, λ=0.002846 Å, T=0.7 μs
E=100 keV: v=4.4×10$^6$ m/sec, λ=0.0009 Å, T=0.23 μs The velocity (v) can be calculated by dividing a setup length between a neutron-source and the present neutron detector by an observed TOE. The kinetic energy (E) can be determined from the velocity (v) using the formula (1).

As the above setup length according to the present invention is usually 2 m~3 m, the measurement of TOF according to the present invention can be performed in the range of 0.1 μs~200 μs.

As described above, the present invention is the 2-D-TOF-pulse neutron detector comprising a GEM-detector including a drift-electrode covered with a neutron-converting material layer to generate electric field, plural GEM-boards covered with a neutron-converting material layer and a 2-D-TOF readout electrode to readout electron, which is put in a chamber filled with electrolytic-dissociative gas, a 2-D-TOF readout electronic circuit board and an image processor.

The above drift-electrode covered with a neutron-converting material layer is set at the uppermost part of the GEM-detector and is able to convert neutron into radiation by nuclear reactions between neutron and the neutron-converting material. For the neutron-converting material, the alkali element such as Li, the alkali-earth element such as Be, the XIII-family element such as B, the XVIII-family element such as He and the heavy metal element from the III-family element to the XII-family element can be used, wherein, $^{10}$B is preferable because $^{10}$B reacts with relatively low-energy neutron with ease due to its large neutron capture cross-section and is scarcely radio-activated by irradiation of neutron. When $^{10}$B is used for the neutron-converting material, α-ray and Li-nucleus are radiated in opposite direction to each other.

For the above neutron-converting material, for example, various compounds such as oxide of $^{10}$B, nitride of $^{10}$B, carbide of $^{10}$B, silicide of $^{10}$B, boride of $^{10}$B and salts of $^{10}$B can be used in addition to $^{10}$B-elemental substance. $^{10}$B is a stable B-element having an isotope-ratio of about 20%. In the present invention, a content-percentage of $^{10}$B is not limited, usually 20% or more, and preferably 99% or more.

The neutron converting material layer covering the drift-electrode is able to increase conversion of neutron with increasing the thickness of the layer, but radiation generated by the nuclear reactions turns to be easily trapped in the inside of the layer. Therefore, the layer is better to have a suitable thickness. The layer is preferably in the range of 1 μm~0.1 μm in thickness, because the projection of radiation into the electrolytic-dissociative gas remarkably decreases when the thickness is more than 1 μm and the conversion of neutron remarkably decreases when the thickness is less than 0.1 μm. The layer with the desirable thickness can be formed onto the drift-electrode, for example, by vapor deposition and the like.

The above neutron-converting material layer is preferably formed in the surface of the drift-electrode in order to make α-ray, of which range is about 1 μm in length, fly out into electrolytic-dissociative gas. By collision between electrolytic-dissociative gas and α-ray, primary electron is emitted.

For the material used for the above drift-electrode, for example, graphite, diamond, aluminum, copper, silver and gold can be used. As the material, graphite, diamond and aluminum are preferable due to their scarce radio-activation property against irradiation of neutron, in particular, graphite and diamond are more preferable due to their superior electrical conductivity.

For the electrolytic-dissociative gas filled in the chamber, noble gas such as Xe, Ar and He gas can be used. As the gas, Ar gas is preferable due to relatively abundant. The other non-combustible gas such as carbon dioxide gas with content of as much as 30% can be preferably added to the electrolytic-dissociative gas in order to make the electrolytic-dissociation of gas stable.

The above GEM-board covered with a neutron-converting material has microscopic through-pores, which is able to convert neutron into radiation such as α-ray with high conversion and successively multiply electron-emission by passing the a-induced primary electron in a high electric field formed in the microscopic through-pores. Such multiplication of chain event is performed with each GEM-board, accordingly electron-emission is multiplied by $10^5$ times or more, leading to the highly sensitive detection of neutron. The characteristic of the present GEM-board is that the surface of GEM is covered with neutron-converting material such as $^{10}$B. The present GEM-board is able to detect neutron, on the other hand the conventional GEM-board disclosed in the patent documents 1-3 detects y-ray and X-ray.

The neutron-converting material layer covering the GEM-board is able to increase conversion of neutron with increasing the thickness of the layer, but radiation generated by the nuclear reactions turns to be easily trapped in the inside of the layer. Therefore, the layer is better to have a suitable thickness. The layer is preferably in the range of 1 µm~0.1 µm in thickness, because the projection of radiation into the electrolytic-dissociative gas remarkably decreases when the thickness is more than 1 µm and the conversion of neutron remarkably decreases when the thickness is less than 0.1 µm. The layer with the desirable thickness can be formed onto the GEM-board, for example, by vapor deposition and the like.

The 2-D position-resolution of the GEM-detector according to the present invention is preferably 0.5 mm or less. Microscopic through-pores of the GEM-board are better to have a suitable pore-size because the pore-size influences the position-resolution and multiplication of GEM. The GEM-board according to the present invention has microscopic through-pores of preferably 70 µm~20 µm in diameter which are aligning at intervals of preferably 140 µm~40 µm, more preferably 50 µm~20 µm in diameter which are aligning at intervals of more preferably 100 µm~40 µm, because the position-resolution of GEM remarkably decreases when the diameter of through-pores is more than 70 pm and the processing of microscopic through-pores is very difficult when the diameter of through-pores is less than 20 µm. By this way, the GEM-board according to the present invention is able to detect neutron with a position-resolution of 0.5 mm or less. On the other hand, the conventional GEM-board usually has microscopic through-pores of 70 µm in diameter which are aligning at intervals of 140 µm and has the position-resolution of 1 mm. Due to the difficult micro-fabrication processing of the conventional GEM-board, it has been very difficult to drill microscopic through-pores less than 70 µm in diameter which are aligning at intervals less than 140 µm. However, the present inventors has achieved the preparation of the GEM-board having microscopic through-pores of 70 µm~20 µm in diameter which are aligning at intervals of 140 µm~40 µm using high-intensity laser.

The above GEM-board is put in the chamber at suitable intervals, because the interval of the plural GEM-boards influences the position-resolution. The interval between the neighboring GEM-boards is preferably in the range of 1.5 mm~0.5 mm, because the position-resolution remarkably decreases when the interval is more than 1.5 mm and the inhibition of discharge is very difficult when the interval is less than 0.5 mm. The conventional GEM-board has been usually put in a chamber at intervals of 2 mm~3 mm due to the technical limitation for the inhibition of discharge. The present GEM-board can be put in the chamber at intervals of 1.5 mm~0.5 mm by inserting a high-resistance of thin layer between the 2-D-TOF readout electrode and the bottom GEM-board which has no neutron-converting material layer in order to load high voltage for increasing multiplication of GEM.

The numbers of the GEM-board according to the present invention are not limited. For example, four pieces of GEM-boards are able to detect neutron by a 10% detection ratio and ten pieces of GEM-boards are able to detect neutron by a 50% detection ratio. Therefore, ten pieces of GEM-board or more are preferable.

The voltage loaded between the neighboring GEM-boards according to the present invention is usually 150 V~400 V and the electric field strength loaded around the microscopic through-pores of the GEM-board is usually 30 kVcm$^{-1}$~80 kVcm$^{-1}$.

The 2-D-TOF readout electrode according to the present invention is able to detect a 2-D position of electron coming out from the bottom GEM-board. The electron being detected at the 2-D position includes information of hitting hour (stop hour), dose and 2-D incident position of pulse neutron. The 2-D-TOF readout electrode according to the present invention has electrode-devices mounted on the electrode-bars with gridiron alignment and is connected with the 2-D-TOF readout integrated circuit through a connector.

The 2-D-TOF readout integrated circuit according to the present invention is able to readout and to calculate electronic information of TOF, dose and 2-D-incident position of pulse neutron which is detected by the 2-D-TOF readout electrode. The 2-D-TOF readout integrated circuit includes at least a 2-D readout electronic circuit to readout TOF, dose and 2-D-incident position of pulse neutron, a time-clock electronic circuit to calculate TOF of pulse neutron and a microprocessor unit to perform highly advanced arithmetic processing of electronic signals including information of TOF, doses, 2-D incident position and transmission image of pulse neutron. The 2-D readout electronic circuit usually mounts ASIC (application specific integrated circuit). The time-clock electronic circuit usually mounts FPGA (field-programmable gate array). The microprocessor unit usually mounts FPGA (field-programmable gate array). ASIC is preferably the one making multi-channel×high-frequency runs possible. FPGA is preferably the one making high-speed arithmetic processing and data compression possible.

Figure 4:
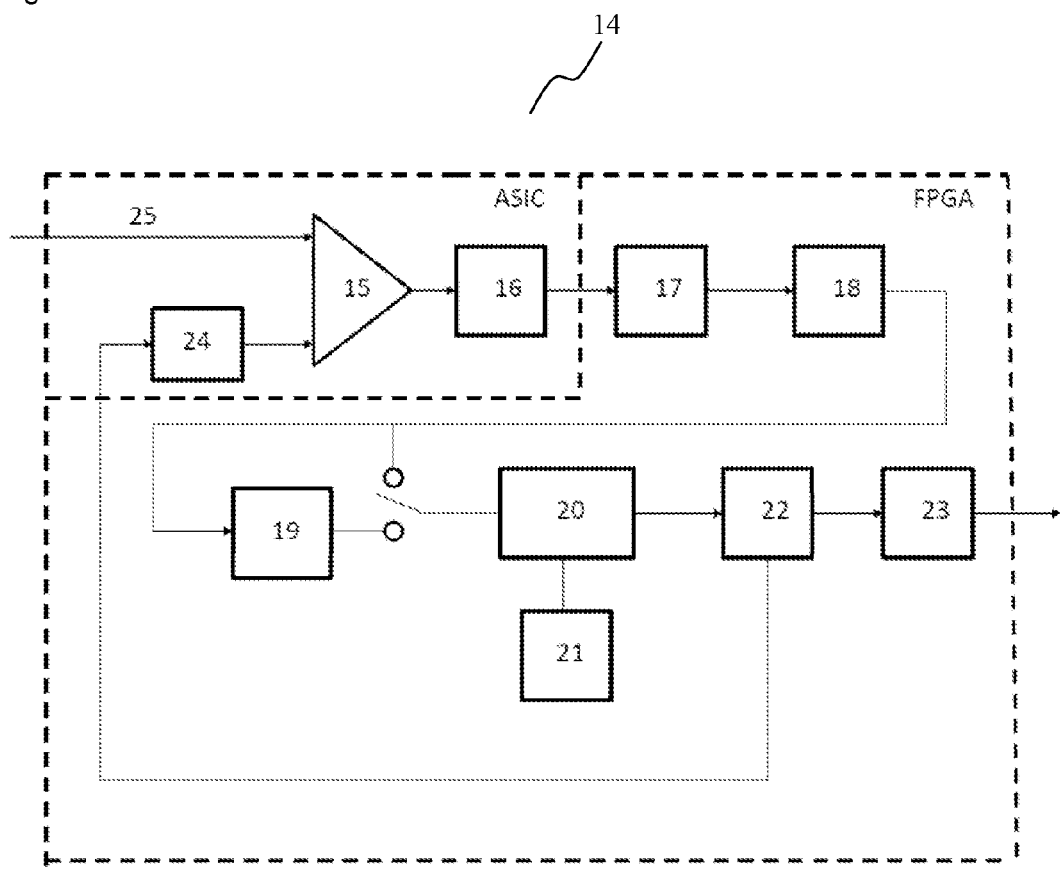
FIG. 4 shows a schematic diagram illustrating the 2-D-TOF readout integrated circuit according to the present invention.

FIG. 4 shows a schematic diagram of the 2-D-TOF readout integrated circuit according to the present invention which is loaded on an ASIC board and FPGA board. An electric signal (25) being detected by the 2-D-TOF readout electrode is transmitted to an ASD (amp-shaper-discriminator) circuit (15) in the ASIC board, transformed into a digital signal and transmitted to the devices in the FPGA board through a LVDS (low-voltage differential signaling) driver (16) of the ASIC board. The FPGA board mounts at least a LVDS receiver (17), sampler (18), event filter (19), event data generator (20), time-clock electronic circuit (21), microprocessor unit (22), Ethernet physical layer controller (23), and the like. In the FPGA board, a digital signal from the LVDS driver (16) is received by the LVDS receiver (17), sampled usually with a sampling frequency of 100 MHz of the sampler (18). Two paths, a bypath in which the signal being sampled by the sampler (18) is transmitted to the event data generator (20) through the event filter (19) and a direct path in which the signal being sampled by the sampler (18) is directly transmitted to the event data generator (20), are formed in the FPGA board. In the former path, the positions of hit events being detected by the 2-D-TOF readout electrode are defined by the event filter (19). This is referred to as a coincidence mode. In the coincidence mode, selected hit signals are only received. For example, in the coincidence mode, for multi-hit events occurring at certain interval, they are excluded by the event filter (19), for multi-hit events occurring at adjacent interval, the center is defined as the hit position. In the latter path, continuous hit events are received until all hits disappear. This is referred to as an all mode. The all mode is useful for designing an event selection algorithm. On the other hand, the coincidence mode has an advantage of high speed data taking because the data size per event in the coincidence mode is smaller than that in the all mode. The hit signal being in the event data generator (20) is attached with the TOF information with a resolution of 10 ns by the time-clock electronic circuit (21), transmitted to the microprocessor unit (22) to data-process thereby, transmitted to the Ethernet physical layer controller (23), and transmitted to the computer through the Ethernet cable. In parallel, a portion of signals in the microprocessor unit (22) is returned to the ASD circuit (15) through the DAC (digital-to-analog converter) (24) in the ASIC board.

The above time-clock electronic circuit is able to calculate the above hitting time (stop hour). At the same time, electronic signals of a zero hour (start hour) of pulse neutron shot from a neutron-source are transmitted to the time-chock electronic circuit. Therefore, the time-clock electronic circuit is able to obtain TOF from the difference between the start hour and stop hour. The time-clock electronic circuit according to the present invention has an independently free setup characteristic function which is able to freely setup the TOF-range for the TOF-calculation. By this way, the TOF-calculation can be very efficiently performed. The time-clock electronic circuit is able to perform the TOF-calculation of pulse neutron of 1 eV~100 keV in the TOF-range of 0.1 µs~200 µs with a time-resolution of about 10 ns. By this way, the following microprocessor unit is able to perform vast amounts of data processing of the incident $10^8$ neutrons/sec/cm² entering the GEM-detector, within the TOF-measuring time of 0.1 µs~200 µs. This is the very large development for the present invention. The conventional neutron detector which has been disclosed in the non-patent document 1 could not detect neutron in the range of 1 eV~100 keV, because the conventional time-clock TOF-range of 1 ms~23 ms was so much long that such neutron as having very high energy in the range of 1 eV~100 keV and velocity in the range of $1.4 \times 10^4$ m/sec~$4.4 \times 10^6$ m/sec and very short TOF in the range of 0.1 µs~200 µs could not be detected.

Figure 5:
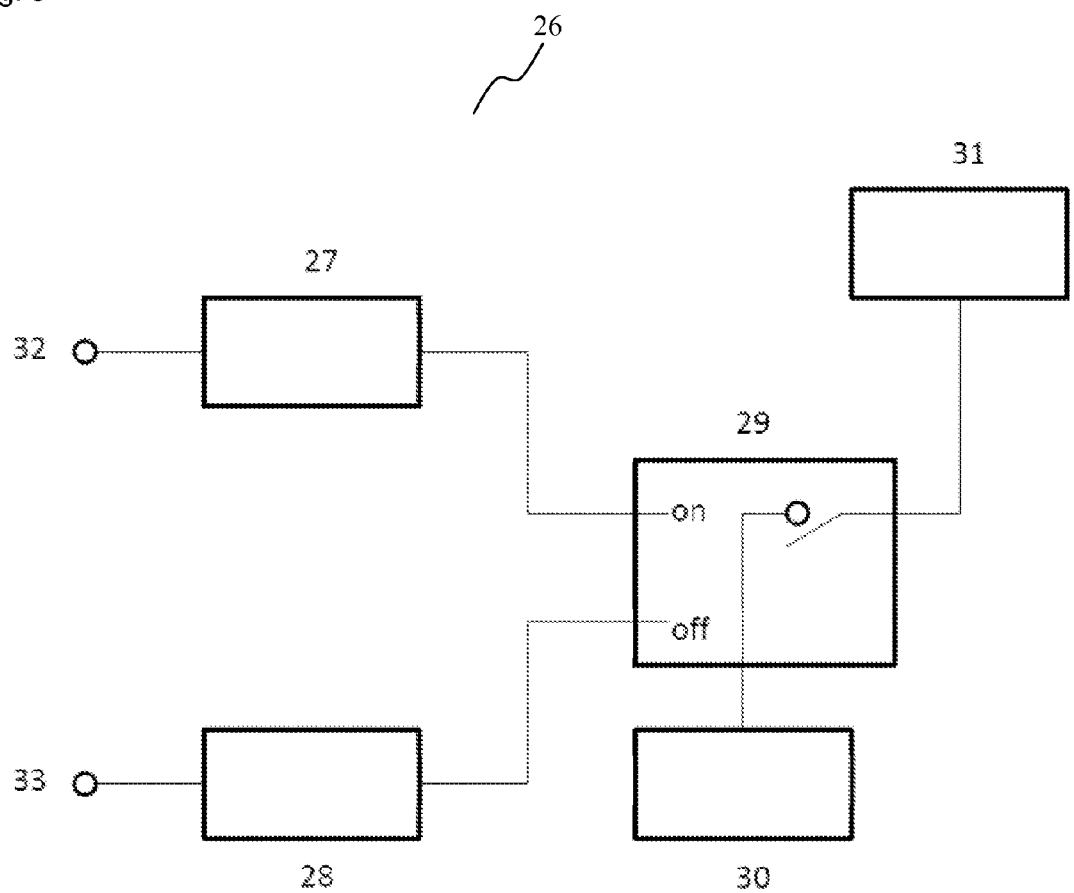
FIG. 5 shows a schematic diagram illustrating an example of the time-clock electronic circuit according to the present invention.

FIG. 5 shows a schematic diagram illustrating an example of the time-clock electronic circuit (21) in the FPGA board as shown in FIG. 4. The time-clock electronic circuit is able to independently setup a TOF-range. The time-clock electronic circuit includes an IC timer (27) to receive a start signal (32), IC timer (28) to receive a stop signal (33), gate (29), clock pulse source (30), electronic pulse counter (31) and the like. The IC timer (27) and IC timer (28) open or close the gate (29) connecting the clock pulse source (30) and the electronic pulse counter (31), respectively. The gate (29) is opened by a certain event (the start signal 32) and closed by another event (the stop signal 33). The TOF is measured by means of counting the number of clock pulse existing in an interval between the start (gate open) and stop (gate close) through the electronic pulse counter (31). The clock pulse is generated by a crystal oscillator usually with a frequency of 100 MHz. The time when the gate (29) is opened or closed can be freely setup by the IC timer (27) or IC timer (28), respectively, that is, the time-clock electronic circuit is functionalized with independent free-setup of a TOF-range. Such a time-clock electronic circuit makes the vast amount of TOF data processing over $10^8$ event/sec/cm² due to pulse neutron of 1 eV~100 keV in the limited TOF-range of 0.1 µs~200 µs by the microprocessor unit (22) in the FPGA board possible. Therefore, the time-clock electronic circuit being functionalized with independent free-setup of a TOF-range is very suitable for the present invention. The time-clock electronic circuit as is used for the present invention is not limited to the time-clock electronic circuit as shown in FIG. 5.

The above 2-D-TOF readout integrated circuit is connected with the image processor to perform image data processing through the Ethernet (registered mark) cable. The image processor is able to perform high-speed image data processing of information transmitted from the 2-D-TOF readout integrated circuit. The image processor according to the present invention mounts GPGPU (general-purpose computing on graphics processing units) and is built in a personal computer. GPGPU is preferably a de fact standard mounting a streaming processer with many calculation units. The image processor is usually built in a personal computer together with software to drive the image processor. By this way, the observed energy spectra and doses of pulse neutron can be displayed on a transmission image of a subject in real-time.

That is, the 2-D-TOF-pulse neutron detector according to the present invention is programmed as the measurement of energy spectra in the range of 1 eV~100 keV, doses, 2-D-incident positions and transmission images can be performed in the TOF range of 1 µs~100 µs and also the result of the measurement can be displayed on the transmission images.

Hereinafter, the present invention will be specially explained as an execution embodiment using the following drawings.

FIG. 1 shows the 2-D-TOF-pulse neutron detector (13) according to the present invention, comprising the GEM-detector (1); the 2-D-TOF readout integrated circuit (6); the image processor (11). The GEM detector includes a drift-electrode (2), plural GEM-boards (3) and 2-D-TOF readout electrode (4) and is put in a chamber filled with electrolytic-dissociative gas. Pulse neutron (5) enters into the chamber in the direction of an arrow. The 2-D-TOF readout integrated circuit (6) includes at least the 2-D-TOF readout electronic circuit (7) mounting ASIC, the time-clock electronic circuit (8) mounting FPGA and the microprocessor unit (9) mounting FPGA. The 2-D-TOF readout integrated circuit (6) is connected with the image processor (11) built in the personal computer (12) through the Ethernet (registered mark) cable (10).

Figure 2:
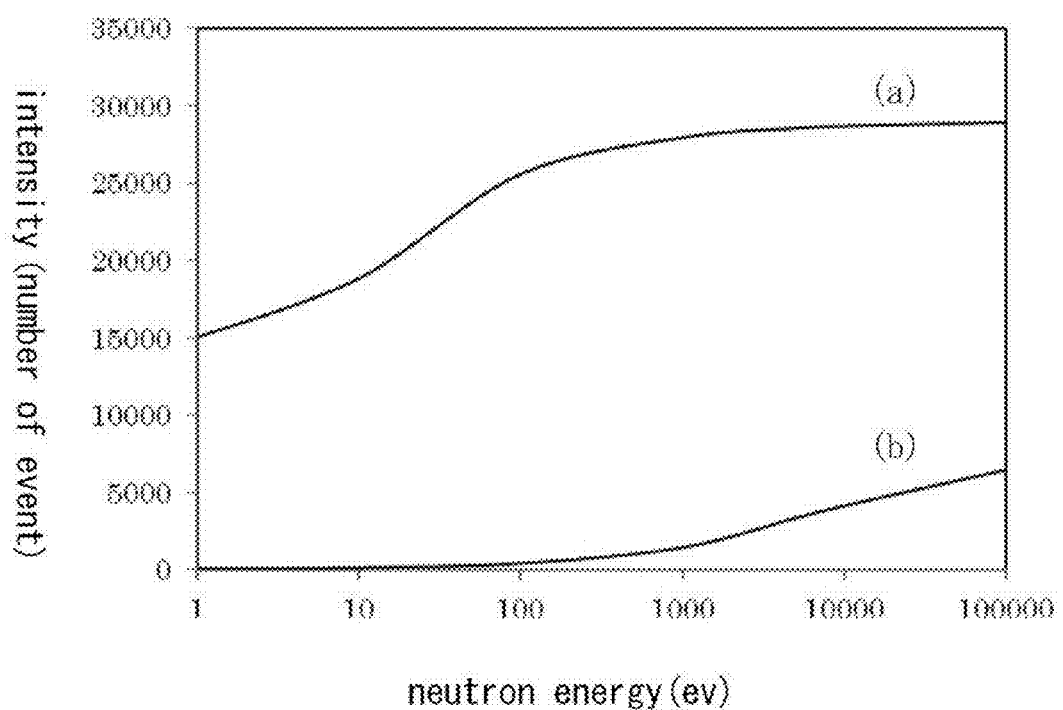
FIG. 2 is an example of the energy spectrum of neutron which was measured with the 2-D-TOF-pulse neutron detector according to the present invention.

FIG. 2 shows an example of an observed energy spectrum which was measured with the 2-D-TOF-pulse neutron detector according to the present invention: (a) is an energy spectrum of neutron being moderated by a moderator; (b) is a transmission energy spectrum of neutron after transmitting a subject which was put in front of the detector. For the subject, a $^{10}$B plate of 1 mm in thickness was used. Neutron was generated by radiating 3 GeV proton beam on a target, moderated by a moderator, and transmitted with a $^{10}$B plate of 1 mm in thickness. The obtained spectrum was smoothed through the deconvolution processing using a law pass filter. The 2-D-TOF-pulse neutron detector was set at a distance of 14 m from the moderator. The TOF was in the range of 3 µs~1000 µs. The abscissa axis of FIG. 2 shows kinetic energy of neutron. The longitudinal axis shows intensity. The intensity of the transmission energy spectrum (b) in the range of 1 eV 100 eV is very weak due to the large neutron capture cross-section of $^{10}$B being used for the subject. The transmission energy spectrum (b) in FIG. 2 well coincides with a simulation of energy spectrum being transmitted with $^{10}$B. The simulation of energy spectrum being transmitted with $^{10}$B can be performed using the neutron capture cross-section of $^{10}$B as given in JENDL-4.0. From FIG. 2, it is found that neutron in the range of 1 eV~100 keV can be measured in a TOF-range of 3 µs~1000 µs. When a distance between the present detector and the moderator is 0.4 m~3 m, a TOF-range is 0.1 μs~200 μs. In this situation, the present detector is able to well detect neutron.

Figure 3:
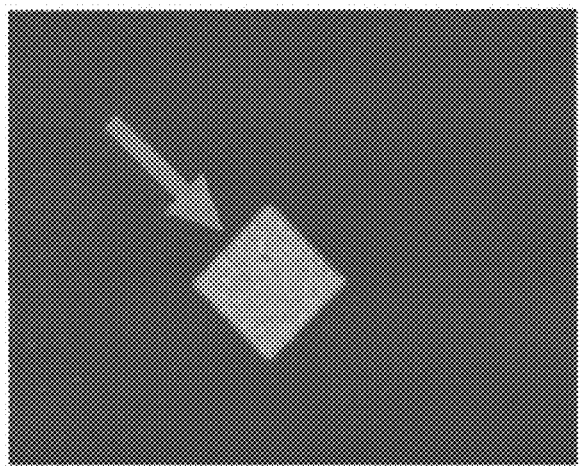
FIG. 3 is an example of the transmission image which was measured with the 2-D-TOF-pulse neutron detector according to the present invention.

FIG. 3 shows an example of the transmission image of a subject. An arrow in FIG. 3 shows the subject. For the subject, the same $^{10}$B plate as that for FIG. 2 was used. From FIG. 3, it is found that the distinct 2-D transmission image can be obtained. The present invention is also able to obtain a distinct 2-D transmission image of a subject containing, for example, biological macromolecules, minerals, light element and the like, with transmission neutron dependent upon substance-specific resonance absorption of neutron.

A summary is: the present invention is able to measure energy spectra of pulse neutron in the range of 1 eV 100 keV and 2-D transmission image of a subject in the TOF-range of 0.1 μs~200 μs. The present invention is also very useful for measuring a distinct transmission image of a subject containing biological macromolecules, minerals, light element and the like with transmission neutron dependent upon substance-specific resonance absorption of neutron.

Industrial Applicability

The present invention has industrial applicability as relating to a monitor of pulse neutron for BNCT and the like. The present invention is also useful for a variety of industrial usages such as diagnostic instrument, material analyzer, and the like.

EXPLANATION OF REFERENCES

1: GEM-detector
2: drift-electrode
3: GEM-board
4: 2-D-TOF readout electrode
5: neutron
6: 2D-TOF readout integrated circuit
7: 2-D-TOF readout electronic circuit (ASIC)
8: time-clock electronic circuit (FPGA)
9: microprocessor unit (FPGA)
10: Ethernet (registered mark) cable
11: image processor
12: personal computer
13: 2-D-TOF-pulse neutron detector
14: 2-D-TOF-readout integrated circuit
15: ASD circuit
16: LVDS driver
17: LVDS receiver
18: sampler
19: event filter
20: event generator
21: time-clock electronic circuit
22: microprocessor unit
23: Ethernet physical layer controller
24: DAC
25: signal being detected by the 2-D-TOF readout electrode
26: time-clock electronic circuit
27: IC timer
28: IC timer
29: gate
30: clock pulse source
31: electronic pulse counter
32: start signal
33: stop signal

The invention claimed is:

1. A 2-D-TOF-pulse neutron detector, comprising:
a chamber filled with electric-dissociative gas;
a GEM detector having a drift electrode, plural GEM-boards and a 2-D-TOF readout electrode, which is included in the chamber; wherein,
   the drift-electrode to generate electric field is placed at the uppermost part of the GEM detector;
   the GEM-board having microscopic through-pores and neutron-converting material layer on the surface to convert neutron to α-ray and to generate electrons from the electric-dissociative gas through ionization effect of α-ray and successively to multiply the generated electrons in the microscopic through-pores applied with the electric field, is placed under the drift-electrode;
   the 2-D-TOF readout electrode to detect electrons, is placed under the bottom GEM-board;
a 2-D-TOF readout integrated circuit mounting an ASIC-unit, FPGA-unit and time-clock electronic circuit housed in the FPGA, which is connected with the 2-D-TOF readout electrode; wherein,
   the ASIC-unit including a 2-D-TOF readout electronic circuit to readout TOF, dose and 2-D incident position of pulse neutron, is connected with the 2-D-TOF readout electrode;
   the FPGA-unit to perform digital calculation of TOF, dose, 2-D incident position and transmission image, is connected with the ASIC-unit;
   the time-clock electronic circuit to calculate TOF of pulse neutron by means of independent free-setup, is housed in the FPGA;
an image processor to perform high speed-calculation of image data processing;
whereby, the measurement of energy spectra, doses, 2-D-incident positions and transmission image of pulse neutron in the range of 1 eV~100 keV is performed in the TOF-range of 0.1 μs~200 μs, detection of $10^8$ neutrons/sec/cm$^2$ is performed in the TOF-range and displaying the result of the measurements is performed in real-time.

* * * * *